(12) United States Patent
Hirasaka

(10) Patent No.: US 9,212,110 B2
(45) Date of Patent: Dec. 15, 2015

(54) METHOD FOR PRODUCING MIXTURE OF FLUOROALKYL IODIDES

(71) Applicant: DAIKIN INDUSTRIES, LTD., Osaka (JP)

(72) Inventor: Takeomi Hirasaka, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 14/382,615

(22) PCT Filed: Mar. 12, 2013

(86) PCT No.: PCT/JP2013/056721
§ 371 (c)(1),
(2) Date: Sep. 3, 2014

(87) PCT Pub. No.: WO2013/157329
PCT Pub. Date: Oct. 24, 2013

(65) Prior Publication Data
US 2015/0018586 A1    Jan. 15, 2015

(30) Foreign Application Priority Data

Apr. 19, 2012   (JP) ................................. 2012-095848

(51) Int. Cl.

| | | |
|---|---|---|
| *C07C 17/278* | (2006.01) | |
| *B01J 23/72* | (2006.01) | |
| *C07C 17/383* | (2006.01) | |
| *C08F 14/26* | (2006.01) | |
| *B01J 23/02* | (2006.01) | |
| *B01J 23/06* | (2006.01) | |
| *B01J 23/22* | (2006.01) | |
| *B01J 23/32* | (2006.01) | |
| *B01J 23/34* | (2006.01) | |
| *B01J 23/42* | (2006.01) | |
| *B01J 23/46* | (2006.01) | |
| *B01J 23/50* | (2006.01) | |

(52) U.S. Cl.
CPC .............. *C07C 17/278* (2013.01); *B01J 23/72* (2013.01); *C07C 17/383* (2013.01); *C08F 14/26* (2013.01); *B01J 23/02* (2013.01); *B01J 23/06* (2013.01); *B01J 23/22* (2013.01); *B01J 23/32* (2013.01); *B01J 23/34* (2013.01); *B01J 23/42* (2013.01); *B01J 23/462* (2013.01); *B01J 23/50* (2013.01)

(58) Field of Classification Search
CPC ...... C07C 17/278; C07C 17/383; B01J 23/72; B01J 23/22; B01J 23/34; B01J 23/32; B01J 23/50; B01J 23/06; B01J 23/43; B01J 23/462; B01J 23/02
USPC ......................................................... 570/138
See application file for complete search history.

(56) References Cited

U.S. PATENT DOCUMENTS

| 5,639,923 A | 6/1997 | Von Werner |
|---|---|---|
| 2004/0049089 A1 | 3/2004 | Homoto et al. |
| 2004/0116753 A1* | 6/2004 | Funakoshi et al. ............ 570/172 |

FOREIGN PATENT DOCUMENTS

| CA | 2544576 | * 10/2006 |
|---|---|---|
| JP | 8-239336 | 9/1996 |
| JP | 2002-316957 | 10/2002 |
| JP | 2009-73762 | 4/2009 |
| WO | 02/36530 | 5/2002 |
| WO | 02/062735 | 8/2002 |

OTHER PUBLICATIONS

International Search Report issued May 28, 2013 in International (PCT) Application No. PCT/JP2013/056721.

* cited by examiner

*Primary Examiner* — Shailendra Kumar
(74) *Attorney, Agent, or Firm* — Wenderoth, Lind & Ponack, L.L.P.

(57) ABSTRACT

The present invention provides a novel method for producing a mixture of fluoroalkyl iodides with high production efficiency, the method enabling the production of a desired fluoroalkyl iodide with high selectivity. Specifically, the present invention provides a method for producing a mixture of fluoroalkyl iodides represented by formula (I):

$$R_f(CF_2CF_2)_nI \qquad (I)$$

(wherein $R_f$ represents a fluoroalkyl group having 1 to 10 carbon atoms, and n is an integer indicating a degree of polymerization), the degree of polymerization n being m or more (m is an integer of 2 or more) by telomerization in metal catalyst-containing reactors, the method including:

(1) step 1 of reacting a fluoroalkyl iodide represented by formula (III):

$$R_fI \qquad (IX)$$

(wherein $R_f$ is a fluoroalkyl group having 1 to 10 carbon atoms) with tetrafluoroethylene in the presence of a metal catalyst in a first reactor to obtain a first reaction mixture containing a mixture of fluoroalkyl iodides represented by formula (I) wherein the degree of polymerization n is 1 or more;

(2) step 2 of separating the first reaction mixture withdrawn from the first reactor into a first fraction containing a fluoroalkyl iodide or a mixture of fluoroalkyl iodides represented by formula (I) wherein the degree of polymerization n is (m−2) or less, a fluoroalkyl iodide, represented by formula (II), and tetrafluoroethylene, a second fraction containing a fluoroalkyl iodide represented by formula (I) wherein the degree of polymerization n is (m−1), and a third fraction containing a mixture of fluoroalkyl iodides represented by formula (I) wherein the degree of polymerization n is m of more; and (3) step 3 of transferring the second fraction, into a second reactor in which a metal catalyst is present and reacting the second fraction with tetrafluoroethylene in the second reactor to obtain a second reaction mixture containing a mixture of fluoroalkyl iodides represented by formula (I) wherein the degree of polymerization n is m or more.

15 Claims, No Drawings

METHOD FOR PRODUCING MIXTURE OF FLUOROALKYL IODIDES

This application is a 371 of PCT/JP2013/056721, filed on Mar. 12, 2013.

TECHNICAL FIELD

The present invention relates, to a method for producing a mixture of fluoroalkyl iodides.

BACKGROUND ART

Methods for producing a fluoroalkyl iodide by telomerization are known.

Such telomerization is conducted by consecutive reactions between 1-iodoperfluoroethane ($C_2F_5I$) as a telogen and tetrafluoroethylene as a taxogen in a reactor.

For example, Patent Literature (PTL) 1 discloses a process for producing a fluoroalkyl iodide represented by $R_f$—$(CF_2CF_2)_n$—I (wherein $R_f$ is a fluoroalkyl group having 1 to 6 carbon atoms, and n is an integer of 1 to 4) by telomerizing a compound represented by the formula $R_f$—I (wherein $R_f$ is a fluoroalkyl group having 1 to 6 carbon atoms) as a telogen and tetrafluoroethylene as a taxogen in a reactor in which a catalyst is present.

While such a method is excellent, there is room, for improvement in terms of selectivity of the fluoroalkyl iodide produced. Specifically, telomerization is conducted by consecutive reactions; therefore, as the reaction of 1-iodoperfluoroethane ($C_2F_5I$) with tetrafluoroethylene progresses, the reaction of a telogen represented by the above formula wherein n is 1 or more with tetrafluoroethylene also proceeds. The rate of reacting 1-iodoperfluoroethane ($C_2F_5I$) with tetrafluoroethylene is slow; therefore, this reaction is a rate-determining step. Accordingly, while 1-iodoperfluoroethane ($C_2F_5I$) is reacted with tetrafluoroethylene to produce 1-iodoperfluorobutane ($C_4F_9I$), the obtained 1-iodoperfluorobutane ($C_4F_9I$) reacts with tetrafluoroethylene in the reactor, and consecutive reactions take place progressively. For example, when the desired fluoroalkyl iodide is 1-iodoperfluorohexane ($C_6F_{13}I$), many other fluoroalkyl iodides that have more carbon atoms than 1-iodoperfluorohexane ($C_6F_{13}I$) are also produced, which results in low selectivity of the desired fluoroalkyl iodide.

To solve this problem, a production method has been proposed in which 1-iodoperfluoroethane ($C_2F_5I$) is reacted with tetrafluoroethylene in a first reactor, after which 1-iodoperfluorobutane ($C_4F_9I$) is separated from the obtained reaction mixture and transferred into a second reactor, and tetrafluoroethylene is added thereto to allow a reaction for producing a fluoroalkyl iodide having more carbon atoms than 1-iodoperfluorobutane ($C_4F_9I$) to proceed in the second reactor (see, for example, Patent Literature (PTL) 2).

While such a method is also excellent, the method produces by-products represented by $R_f$—$(CF_2CF_2)_n$—H (wherein $R_f$ is any one of fluoroalkyl groups having 1 to 10 carbon atoms, and n is an integer indicating a degree of polymerization) due to the use of a peroxide as a catalyst for promoting the reaction, and the method requires a step of removing the by-products from the reaction system, which results in low production efficiency.

Thus, there is a need for a new method of producing a mixture of fluoroalkyl iodides with high production efficiency, the method enabling the production of a desired fluoroalkyl iodide with high selectivity.

CITATION LIST

Patent Literature

PTL 1: WO2002/036530
PTL 2: WO2002/062735

SUMMARY OF INVENTION

Technical Problem

An object of the present invention is to provide a novel method for producing a mixture of fluoroalkyl iodides with high production efficiency, the method enabling the production of a desired fluoroalkyl iodide with high selectivity.

Solution to Problem

As a result of extensive research to achieve the above 1.5 object, the present inventors found that the above object can be achieved by producing a mixture of fluoroalkyl iodides by a method comprising:
(1) step 1 of reacting a fluoroalkyl iodide represented by formula (II):

$$R_fI \qquad (II)$$

(wherein $R_f$ is a fluoroalkyl group having 1 to 10 carbon atoms) with tetrafluoroethylene in the presence of a metal catalyst in a first reactor to obtain a first reaction mixture;
(2) step 2 of separating the first reaction mixture withdrawn from the first reactor into
a first fraction containing a fluoroalkyl iodide or a mixture of fluoroalkyl iodides represented by formula (I) wherein the degree of polymerization n is (m−2) or less, a fluoroalkyl iodide represented by formula (II), and tetra fluoroethylene;
a second fraction containing a fluoroalkyl iodide represented by formula (I) wherein the degree of polymerization n is (m−1); and
a third fraction containing a mixture of fluoroalkyl iodides represented by formula (I) wherein the degree of polymerization n is m or more; and
(3) step 3 of transferring the second fraction into a second reactor in which a metal catalyst is present and reacting the second fraction with tetrafluoroethylene in the second reactor. The present invention has been accomplished based on this finding.

Specifically, the present invention provides the following methods for producing a mixture of fluoroalkyl iodides by telomerization.
1. A method for producing a mixture of fluoroalkyl iodides represented by formula (I):

$$R_f(CF_2CF_2)_nI \qquad (I)$$

(wherein $R_f$ represents a fluoroalkyl group having 1 to 10 carbon atoms, and n is an integer indicating a degree of polymerization), the degree of polymerization n being m or more (m is an integer of 2 or more)
by telomerization in metal catalyst-containing reactors, the method comprising:
(1) step 1 of reacting a fluoroalkyl iodide represented by formula (II):

$$R_fI \qquad (II)$$

(wherein $R_f$ is a fluoroalkyl group having 1 to 10 carbon atoms) with tetrafluoroethylene in the presence of a metal catalyst in a first reactor to obtain a first reaction mixture containing a mixture of fluoroalkyl iodides represented by formula (I) wherein the degree of polymerization n is 1 or more;

(2) step 2 of separating the first reaction mixture withdrawn from the first reactor into a first fraction containing a fluoroalkyl iodide or a mixture of fluoroalkyl iodides represented by formula (I) wherein the degree of polymerization n is (m−2) or less, a fluoroalkyl iodide represented by formula (II), and tetrafluoroethylene, a second fraction containing a fluoroalkyl iodide represented by formula (I) wherein the degree of polymerization n is (m−1), and a third fraction containing a mixture of fluoroalkyl iodides represented by formula (I) wherein the degree of polymerization n is m or more; and (3) step 3 of transferring the second fraction into a second reactor in which a metal catalyst is present and reacting the second fraction with tetrafluoroethylene in the second reactor to obtain a second reaction mixture containing a mixture of fluoroalkyl iodides represented by formula (I) wherein the degree of polymerization n is m or more.

2. The method according to Item 1, which produces a mixture of fluoroalkyl iodides represented by formula (I) wherein $R_f$ represents $C_2F_5$ and n is 2 or more.

3. The method according to Item 1 or 2, wherein step 1 further comprises returning the first fraction separated in step 2 to the first reactor to supply one or more types of fluoroalkyl iodides represented by formula (I) wherein the degree of polymerization n is (m−2) or less and tetrafluoroethylene, and reacting the one or more types of fluoroalkyl iodides with the tetrafluoroethylene.

4. The method according to any one of Items 1 to 3, further comprising step 4 of separating the second reaction mixture obtained in step 3 into a fourth fraction containing a fluoroalkyl iodide or a mixture of fluoroalkyl iodides represented by formula (I) wherein the degree of polymerization n is (m−1) or less, and tetrafluoroethylene, a fifth fraction containing a fluoroalkyl iodide represented by formula (I) wherein the degree of polymerization n is m, and a sixth fraction containing a mixture of fluoroalkyl iodides represented by formula (I) wherein the degree of polymerization n is (m+1) or more.

5. The method according to Item 4 wherein the third fraction separated in step 2 is subjected to step 4 together with the second reaction mixture to supply to step 4 a mixture of fluoroalkyl iodides represented by formula (I) wherein the degree of polymerization n is m or more.

6. The method according to Item 4, wherein when a cycle comprising subjecting the second fraction to steps 3 and 4 to obtain a fifth fraction, which is a next fraction, is defined as one cycle, the next fraction obtained by the cycle is further subjected to the same steps as steps 3 and 4 to thereby repeat the cycle p times (p is an integer of 1 or more).

7. The method according to any one of Items 1 to 6, wherein the metal catalyst is at least one member selected from the group consisting of copper, zinc, magnesium, vanadium, rhenium, rhodium, ruthenium, platinum, silver, and these metals with a small amount of a transition metal added thereto.

The production method of the present invention is described in detail below.

The production method of the present invention is characterized in that it is a method for producing a mixture of fluoroalkyl iodides by telomerization in metal catalyst-containing reactors, each of the fluoroalkyl iodides being represented by formula (I)

$$R_f(CF_2CF_2)_nI \quad\quad (I)$$

(wherein $R_f$ represents a fluoroalkyl group having 1 to 10 carbon atoms, and n is an integer indicating a degree of polymerization) wherein n is m (m is an integer of 2 or more) or more, the method comprising:

(1) step 1 of reacting a fluoroalkyl iodide represented by formula (II):

$$R_fI \quad\quad (II)$$

(wherein $R_f$ is a fluoroalkyl group having 1 to 10 carbon atoms) with tetrafluoroethylene in a first reactor to obtain a first react ion mixture containing a mixture of fluoroalkyl iodides represented by formula (I) wherein n is 1 or more;

(2) step 2 of separating the first reaction mixture withdrawn from the first reactor into a first fraction containing a fluoroalkyl iodide or a mixture of fluoroalkyl iodides represented by formula (I) wherein n is (m−2) or less, a fluoroalkyl iodide represented by formula (II), and tetrafluoroethylene, a second fraction containing a fluoroalkyl iodide represented by formula (I) wherein n is (m−1), and a third fraction containing a mixture of fluoroalkyl iodides represented by formula (I) wherein n is m or more; and (3) step 3 of reacting the second fraction with tetrafluoroethylene in a second reactor to obtain a second reaction mixture containing a mixture of fluoroalkyl iodides represented by formula (I) wherein the degree of polymerization n is m or more.

According to the production method of the present invention having the above characteristics, a metal catalyst is used for telomerization, which inhibits the production of by-products represented by $R_f$—$(CF_2CF_2)_n$—H (wherein $R_f$ is any one of fluoroalkyl groups having 1 to 10 carbon atoms, and n is an integer indicating a degree of polymerization). Accordingly, no step for removing by-products is required in a reaction system using a plurality of reactors as in the present invention, thus inhibiting reduction of production efficiency.

Further, because a plurality of reactors are used in the production method of the present invention, the proportion of fluoroalkyl iodides having higher degrees of polymerization n in the first reaction mixture in the first reactor can be reduced by performing the reaction of 1-iodoperfluoroethane ($C_2F_5I$) with tetrafluoroethylene, which is a slow reaction, in the first reactor. In the second reactor, a telomerization reaction using as a starting material a fluoroalkyl iodide with the degree of polymerization n of 1 or more, which is a reaction faster than the reaction performed in the first reactor, such as a step of reacting 1-iodoperfluorobutane ($C_4F_9I$) with tetrafluoroethylene to obtain 1-iodoperfluorohexane ($C_6F_{13}I$), can be performed. Thus, the telomerization reaction using a fluoroalkyl iodide with the degree of polymerization n of 1 or more as a starting material, which is a fast reaction, can be performed independently from the slow reaction performed in the first reactor. Therefore, the reaction time can be suitably adjusted to increase the selectivity of a desired fluoroalkyl iodide, such as 1-iodoperfluorohexane ($C_6F_{13}I$).

The present invention provides a method for producing a mixture of fluoroalkyl iodides that are obtained by telomerization using 1-iodoperfluoroethane ($C_2F_5I$) as a telogen and tetrafluoroethylene (hereinafter sometimes referred to as "TFE") as a taxogen, and represented by $C_2F_5(CF_2CF_2)_nI$ (n is an integer indicating a degree of polymerization) wherein the degree of polymerization n is 2 or more (specifically, 1-iodoperfluorohexane ($C_6F_{13}I$; n=2), 1-iodoperfluorooctane ($C_8F_{17}I$; n=3), 1-iodoperfluorodecane ($C_{10}F_{21}I$; n=4), 1-iodoperfluorododecane ($C_{12}F_{25}I$; n=5), 1-iodoperfluorotetradecane ($C_{14}F_{29}I$; n=6), and the like), preferably in such a manner that the mixture contains 1-iodoperfluorohexane ($C_6F_{13}I$; n=2) in the largest proportion.

The fluoroalkyl iodides produced by the production method of the present invention are compounds represented by formula (I). In formula (I), $R_f$ represents any one of fluoroalkyl groups having 1 to 10 carbon atoms. $R_f$ corresponds to the fluoroalkyl group of fluoroalkyl iodide used as a starting material for the telomerization.

The mixture of fluoroalkyl iodides means a mixture of a plurality of fluoroalkyl iodides that have different degrees of polymerization n.

The object to be produced by the production method of the present invention is a mixture of fluoroalkyl iodides whose individual degrees of polymerization n are m or more, and is a mixture of fluoroalkyl iodides whose individual degrees of polymerization are m, m+1, m+2, etc. However, depending on the separation conditions for reaction mixtures, etc., this mixture may inevitably contain fluoroalkyl iodides wherein n is less than m, an unreacted fluoroalkyl iodide, etc. It should be noted that a mixture that contains such inevitably contained compounds is also included within the scope of the object to be produced by the production method of the present invention.

When m in formula (I) is 2, a fluoroalkyl iodide or a mixture of fluoroalkyl iodides represented by formula (I) wherein n is (m−2) or less has the degree of polymerization n of 0. This means that the compound represented by formula (I) is a fluoroalkyl iodide represented by $R_fI$.

In the production method of the present invention, m is an integer selected from integers of 2 or more, and can be suitably selected according to the purpose of use of the fluoroalkyl iodide, etc. In the mixture of fluoroalkyl iodides wherein n is m or more, the degree of polymerization of the fluoroalkyl iodide having the maximum degree of polymerization n max varies depending on the telomerization conditions, Generally, n max is about 20. The mixture obtained by the production method of the present invention preferably contains a fluoroalkyl iodide with the degree of polymerization n of m in the largest proportion.

The method for producing a mixture of fluoroalkyl iodides according to the present invention is characterized in that two reactors are used and that the method comprises reacting a fluoroalkyl iodide represented by the formula: $R_fI$ (wherein $R_f$ represents any one of fluoroalkyl groups having 1 to 10 carbon atoms) with TFE in a first reactor to obtain a mixture of fluoroalkyl iodides, separating a fluoroalkyl iodide whose degree of polymerization n is (m−1) from the mixture, and reacting the fluoroalkyl iodide with TFE in a second reactor. The use of the second reactor makes it possible to increase the proportion of the fluoroalkyl iodide with the degree of polymerization of m in the product (that is, in a mixture of fluoroalkyl iodides whose degrees of polymerization n are m or more).

In the production method of the present invention, there is no particular limitation on the shape, etc., of the first and second reactors, and any reactor conventionally used for a telomerization reaction (for example, autoclaves) can be used. Further, the production method of the present invention can be carried out by a simple operation.

Metal Catalyst

As the metal catalyst, for example, a metal catalyst of a specific quality in a predetermined amount is introduced into each reactor before starting the reaction. The amount of the metal catalyst introduced in the first reactor and second reactor is preferably 0.001 to 1 mole per mole of fluoroalkyl iodide ($R_fI$).

When the metal catalyst is a copper powder, the catalyst particles have a particle size of 0.1 µm to 1 mm, preferably 20 µm to 0.3 mm, and a mean particle size of 20 µm to 200 µm, preferably 45 µm to 100 µm. The particle shape is not particularly limited. For example, the particles may have various shapes, such as a shape obtained by subjecting a copper ingot to physical processing such as cutting and pulverization, or a particle shape obtained by electrical and/or chemical deposition from a copper ion-containing electrolyte. As such a copper powder, for example, a copper powder called primary copper powder 325 mesh, which is commercially available as a reagent from Kishida Chemical Co., Ltd., can be used.

As the metal catalyst, other metal materials that can substantially catalyze the telomerization to be conducted in the present invention can also be used. Examples of such materials include zinc, magnesium, vanadium, rhenium, rhodium, ruthenium, platinum, silver, and these metals with a small amount of a transition metal, such as alloys of such compositions, added thereto. When a mixture of such a material with the above copper powder does not adversely affect the telomerization of the present invention, the mixture can also be used as the catalyst. When a material other than copper powder is used or a mixture of copper powder with a material other than copper powder is used as a catalyst, such a catalyst is also required to have the particle size and mean particle size described above for copper powder.

Step 1

Step 1 is a step of carrying out a telomerization reaction in the first reactor in which a metal catalyst is present. The telomerization reaction is carried out by reacting a fluoroalkyl iodide represented by formula (II):

$$R_fI \qquad (II)$$

with TFE. In formula (II), $R_f$ is any one of fluoroalkyl groups having 1 to 10 carbon atoms. $R_f$ is preferably any one of fluoroalkyl groups having 1 to 8 carbon atoms, more preferably any one of fluoroalkyl groups having 1 to 5 carbon atoms, and particularly preferably a fluoroalkyl group having 2 carbon atoms.

Examples of fluoroalkyl iodides represented by formula (II) include iodotrifluoromethane ($CF_3I$), 1-iodoperfluoroethane ($C_2F_5I$), 2-iodoperfluoropropane ($CF_3CFICF_3$), and 1-iodoperfluorobutane ($C_4F_9I$). Of these, 1-iodoperfluoroethane ($C_2F_5I$) is generally used for telomerization of TFE. 1-Iodoperfluoroethane ($C_2F_5I$) is also preferably used in the production method of the present invention.

In step 1, the telomerization reaction may be carried out under conditions that are conventionally used in the production of fluoroalkyl iodides. Specifically, the reaction temperature may be set between 30 and 150° C., and the reaction pressure may be set between 0.01 and 2 MPa to allow the reaction to proceed. The reaction time is generally in the range of 0.1 to 10 hours. The reaction pressure is a pressure generated by TFE, which is forced into the reactor. The specific pressures described above are gauge pressures. In this specification including the descriptions hereinafter, pressure is indicated by gauge pressure unless otherwise specified.

In the first reactor, the molar ratio of the fluoroalkyl iodide ($R_fI$) represented by formula (II) to tetrafluoroethylene: (TFE) is preferably in the range of 20:80 to 99:1. Generally, as the $R_fI$/TFE ratio is higher (that is, as the molar ratio of TFE is lower), n max of the obtained mixture of fluoroalkyl iodides is lower and the average degree of polymerization n ave of the mixture is lower. Therefore, it is preferable that the $R_fI$/TFE ratio is higher when a lower n max and a lower n ave are desired in the ultimately obtained mixture of fluoroalkyl iodides. For example, when 1-iodoperfluoroethane ($C_2F_5I$) is used as $R_fI$ to produce a mixture of fluoroalkyl iodides whose individual degrees of polymerization n are 2 or more, a mixture whose n ave is closer to 2 (for example, about 2.03 to 2.30) can be obtained as a product by carrying out the production method of the present invention with $R_fI$:TFE (molar ratio) in the range of 99:1 to 97:3.

In the first reactor, TFE is fed to a vapor phase of the reactor. Alternatively, TFE may be fed to $R_fI$ of the liquid phase so that bubbles are generated.

The fluoroalkyl iodide(s) wherein the degree of polymerization n is (m−2) or less may be, for example, fluoroalkyl iodide (s) obtained by separating the first reaction mixture in step 2 described below. That is, one or more types of fluoroalkyl iodides with n of (m−2) or less may be supplied by returning a portion, of the first reaction mixture. In this case, the first fraction separated by step 2 described below is returned to the first reactor to thereby supply one or more types of fluoroalkyl iodides represented by formula (I) wherein n is (m−2) or less and tetrafluoroethylene, and react the e one or more types of fluoroalkyl iodides with the tetrafluoroethylene.

The fluoroalkyl iodide(s) with n of (m−2) or less that are supplied into the first reactor do not always need to be those that are obtained by telomerization of $R_fI$ with TFE. Any compound that is obtained, by a method other than telomerization may also be supplied into the first reactor as long as the compound has a structure that is represented by formula (I) with n of (m−2) or less. Although such compounds cannot exactly be called "fluoroalkyl iodides," such compounds are also called "fluoroalkyl iodides" for convenience in this specification.

Step 2

Next, step 2 is described. Step 2 is a step in which the first reaction mixture containing a, mixture of fluoroalkyl iodides whose individual degrees of polymerization n are 1 or more is separated into three fractions that individually contain the above components. However, each fraction may contain other components (for example, fluoroalkyl iodides that should be contained in the other fractions) in addition to the above components, as long as such other components do not adversely affect the production of the mixture of fluoroalkyl iodides according to the present invention. Such other components may be inevitably contained depending on the property of the apparatus used for the separation and the operation conditions. Each fraction is described below.

The first fraction contains a low-polymerization-degree fluoroalkyl iodide or a mixture of such fluoroalkyl iodides represented by formula (I) wherein the degree of polymerization n is (m−2) or less, an unreacted fluoroalkyl iodide represented by the formula $R_fI$, and tetrafluoroethylene. The first fraction contains unreacted TFE in the form of a vapor phase and/or a liquid phase. The first fraction is preferably returned to the first reactor from the viewpoint of production efficiency.

In the above, "a fluoroalkyl iodide or a mixture of fluoroalkyl iodides . . . wherein the degree of polymerization n is (m−2) or less" means that depending on the value of m, the number of types of fluoroalkyl iodides whose n is (m−2) or less may be only one, or more than one. For example, when m is 3, the fluoroalkyl iodides wherein n is (m−2) or less are a mixture of two types of fluoroalkyl iodides, i.e., one wherein n is 1, and the other wherein n is 0 (the telogen represented by formula (II): $R_fI$). Alternatively, for example, when m is 2, the fluoroalkyl iodide wherein n is (m−2) or less is only one type of fluoroalkyl iodide wherein n is 0 (the telogen represented by formula (II): $R_fI$), and cannot be a mixture.

The first fraction may contain other components, such as fluoroalkyl iodides wherein the degree of polymerization n is more than (m−2), in addition to the fluoroalkyl iodides with the degree of polymerization n of (m−2) or less, $R_fI$, and TFE. Such other components may be inevitably contained in the first fraction depending on the properties of the separation apparatus, etc., as described above. The amount of other components contained in the first fraction is preferably as small as possible (for example, 0.1 mol % or less).

The second fraction contains a fluoroalkyl iodide represented by formula (I) wherein the degree of n is (m−1), The second fraction is subjected to a telomerization reaction in step 3 described below. The second fraction may contain other components, such as a fluoroalkyl iodide whose degree of polymerization is less than or more than (m−1), in addition to the fluoroalkyl iodide whose degree of polymerization n is (m−1). As described above, such other components may be inevitably contained in the second fraction depending on the properties of the separation apparatus, etc. The amount of other components contained in the second fraction is preferably as small as possible (for example, 0.1 mol % or less).

The third fraction contains a mixture of fluoroalkyl iodides represented by formula (I) wherein the degree of polymerization n is m or more. The third fraction is withdrawn as a desired product. The third fraction may contain other components such as a fluoroalkyl iodide whose degree of polymerization n is (m−1) or less, in addition to the fluoroalkyl iodides with the degree of polymerization n of m or more. Such other components may be inevitably contained in the third fraction depending on the properties of the separation apparatus, etc., as described above. It is preferable that the amount of other components contained in the third fraction is as small as possible (for example, 0.1 mol % or less).

In step 2, the separation into fractions may be performed simultaneously in a single separation apparatus. Alternatively, step 2 may be carried out in two stages. Specifically, step 2 may be carried out by separating the first reaction mixture into a first fraction, and an intermediate fraction containing a second fraction and a third fraction, and then separating the intermediate fraction into the second fraction and the third fraction in another separation apparatus.

Step 2 is preferably carried out by using a distillation column. The distillation column may be a plate column or a packed column. When step 2 is carried out by continuous distillation in a single distillation column, the first fraction is continuously withdrawn from the top of the column, the third fraction is continuously withdrawn from the bottom of the column, and the second fraction is continuously withdrawn from an intermediate position of the column as a side-cut. Alternatively, step 2 may be batch distillation using a single distillation column. In that case, the first fraction and the second fraction are obtained as distillates by being distilled off in this order. The third fraction is obtained as a still residue or as a distillate that is obtained by distillation after the first and second fractions have been distilled off.

In the case where step 2 is carried out in two stages by using two distillation columns, the first fraction is withdrawn from the top of the first distillation column, and the intermediate fraction is withdrawn from the bottom of the first distillation column. The intermediate fraction is sent to the second distillation column and subjected to distillation. The second fraction is withdrawn from the top of the second distillation column, and the third fraction is withdrawn from the bottom of the second distillation column. Each distillation carried out in the first and second distillation columns may be continuous distillation or batch distillation.

Alternatively, step 2 may be carried out by any method other than distillation. For example, step 2 may be carried out by extraction or membrane separation.

Step 3

Next, step 3 is described. Step 3 is a step in which a fluoroalkyl iodide with the degree of polymerization n of (m−1), which is contained in the second fraction obtained in step 2, is reacted with TFE in the second reactor. In step 3, a low-polymerization-degree fluoroalkyl iodide whose n is less than m by one is telomerized to obtain a mixture of fluoroalkyl iodides whose individual degrees of polymerization n are m or more. Step 3 is carried out in the same manner as step 1 by supplying a fluoroalkyl iodide with n of (m−1) and TFE into the second reactor. Therefore, a detailed description of the conditions of step 3 is omitted. The kind and molar ratio of metal catalyst used in the second reactor are the same as those described for the first reactor. The preferable molar ratio of the fluoroalkyl iodide to TFE in the second reactor is the same as the preferable molar ratio of $R_fI$ to TFE described concerning step 1.

Step 4

Next, step 4 is described. Step 4 is a step in which the second reaction mixture obtained in step 3 is separated into a fourth fraction containing a fluoroalkyl iodide or a mixture of fluoroalkyl iodides represented by formula (I) wherein the degree of polymerization n is (m−1) or less, and tetrafluoroethylene, a fifth fraction containing a fluoroalkyl iodide represented by formula (I) wherein the degree of polymerization n is m, and a sixth fraction containing a mixture of fluoroalkyl iodides represented by formula (I) wherein the individual degrees of polymerization n are (m+1) or more.

The second reaction mixture usually contains an unreacted fluoroalkyl iodide or a mixture of unreacted fluoroalkyl iodides wherein n is (m−1) or less, fluoroalkyl iodide(s) wherein n is (m+1) or more, and tetraethylene, in addition to the desired fluoroalkyl iodide wherein n is m. Therefore, the second reaction mixture is preferably separated into a fourth fraction which contains a fluoroalkyl iodide or a mixture of fluoroalkyl iodides represented by formula (I) wherein the degree of polymerization n is (m−1) or less, and tetrafluoroethylene, and a fifth fraction which contains a fluoroalkyl iodide represented by formula (i) wherein the degree of polymerization n is in, and a sixth fraction which contains a mixture of fluoroalkyl iodides represented by formula (I) wherein the degree of polymerization n is (m+1) or more.

The fourth fraction is preferably returned to the second reactor. The fifth fraction is withdrawn as a product.

Step 4 is carried out in the same manner as step 2 by using the second reaction mixture obtained in step 3. Therefore, a detailed description of the conditions of step 4 is omitted. The amount of other components contained in each fraction, separation method, etc., in step 4 are the same as those described concerning step 2.

In step 4, a mixture of fluoroalkyl iodides represented by formula (I) wherein the degree of polymerization n is m or more are preferably supplied to step 4 by subjecting the third fraction separated in step 2 and the second reaction mixture to step 4. This allows recycling of the third fraction separated in step 2, and can efficiently produce a fifth fraction containing a fluoroalkyl iodide represented by formula (I) with the degree of polymerization n of m.

According to the production method of the present invention, as described above, subjecting the second fraction to the above steps 3 and 4 can provide the fifth fraction, which is a next fraction. In the production method of the present invention, when the cycle comprising this series of steps is defined as one cycle, the next fraction obtained in this cycle may be further subjected to the same steps as steps 3 and 4 to repeat the cycle p times (p is an integer of 1 or more).

For example, the second fraction is subjected to the above steps 3 and 4 to produce a fifth fraction (a fraction containing a fluoroalkyl iodide with the degree of polymerization n of m), which is a next fraction. With this cycle being defined as one cycle, when this cycle is repeated once (p=1) by using the fifth fraction, which is the next fraction, an eighth fraction containing a fluoroalkyl iodide with the degree of polymerization n of (m+1), which is a further succeeding fraction, can be obtained.

When the eighth fraction that is a further succeeding fraction is subjected to the above cycle again (p=2), an eleventh fraction containing a fluoroalkyl iodide with the degree of polymerization n of (m+2) can be obtained.

By carrying out each step as described above, a mixture of fluoroalkyl iodides with the degree of polymerization n of m or more can be preferably produced in such a manner that the mixture contains a fluoroalkyl iodide with n of m in a large proportion. The mixture of fluoroalkyl iodides is useful as a starting material for various chemical products, and is particularly suitable for producing a fluorine-containing acrylic acid ester.

Advantageous Effects of Invention

Because a metal catalyst is used for telomerization in the method of the present invention, the production of by-products represented by $R_f$—$(CF_2CF_2)_n$—H (wherein $R_f$ is any one of fluoroalkyl groups having 1 to 10 carbon atoms, and n is an integer indicating a degree of polymerization) can be inhibited. Therefore, no step for removing by-products is required in a reaction system using a plurality of reactors as in the present invention, thus inhibiting reduction of production efficiency.

Because a plurality of reactors are used in the production method of the present invention, the telomerization reaction between 1-iodoperfluoroethane ($C_2F_5$) and tetrafluoroethylene, which is a slow reaction, can be performed to produce 1-iodoperfluorobutane ($C_4F_9I$) in a first reactor, whereas the telomerization reaction using a fluoroalkyl iodide having the degree of polymerization n of 1 or more as a starting material, which is a reaction faster than the reaction performed in the first reactor, such as a step of reacting 1-iodoperfluorobutane ($C_4F_9I$) with tetrafluoroethylene to obtain 1-iodoperfluorohexane ($C_6F_{13}I$), can be performed in another reactor. Thus, the telomerization reaction using a fluoroalkyl iodide having the degree of polymerization n of 1 or more as a starting material, which is a fast reaction, can be performed independently from the slow reaction performed in the first reactor. Therefore, the reaction time can be suitably adjusted to increase the selectivity of a desired fluoroalkyl iodide, such as 1-iodoperfluorohexane ($C_6F_{13}I$).

DESCRIPTION OF EMBODIMENTS

The present invention is specifically described below with reference to Examples and Comparative Examples. However, the present invention is not limited thereto or thereby.

Example 1

A 200 ml-capacity stainless steel pressure reactor equipped with a stirrer was provided as a first reactor. The reactor was charged with 200 g of 1-iodoperfluoroethane ($C_2F_5I$) as a telogen and charged with 10 g of copper powder as a metal catalyst, followed by heating to 100° C. While the temperature in the reactor was maintained at 100° C., tetrafluoroethylene was supplied as a taxogen while stirring the reaction mixture to pressurize the reactor until the pressure in the reactor became 1.2 MPa (gauge pressure).

Then, while the above temperature and pressure conditions were maintained, and while 1-iodoperfluoroethane ($C_2F_5I$) was supplied at a flow rate of 133 g/hr and tetrafluoroethylene was supplied at a flow rate of 5.5 g/hr, a reaction, mixture was discharged from the reactor at a rate of 138.5 g/hr. A telomerization reaction was thereby performed. The obtained reaction mixture was cooled to give 1,255 g of a first reaction mixture.

This reaction mixture was distilled to yield 1,124 g (purity: 99.9 mol %) of 1-iodoperifluoroethane ($C_2F_5I$), 90 g (purity: 99.9 mol %) of 1-iodoperfluorobutane ($C_4F_9I$), 33 g (purity: 99.9 mol %) of 1-iodoperfluorohexane ($C_6F_{13}I$), and 18 g of a fraction containing 1-iodoperfluorooctane ($C_8F_{17}I$).

A 200 ml-capacity stainless steel pressure reactor equipped with a stirrer was provided as a second reactor. The reactor was charged with 90 g of the above-prepared 1-iodoperfluorobutane ($C_4F_9I$) as a telogen and further charged with 4.5 g of copper powder as a metal catalyst. While the second reactor was heated such that the temperature in the reactor was maintained at 100° C., tetrafluoroethylene was supplied as a taxogen while stirring the reaction mixture to pressurize the reactor until the pressure in the reactor became 0.35 MPa (gauge pressure) Since the telomerization reaction consumed tetrafluoroethylene, the reaction was carried out while suitably supplying additional tetrafluoroethylene so as to keep the pressure constant. The supply of tetrafluoroethylene was stopped when a total of 3.3 g of tetrafluoroethylene was supplied. Cooling was performed to give a second reaction mixture.

This reaction mixture was distilled to yield 81 g (purity: 99.9 mol %) of 1-iodoperfluorobutane ($C_4F_9I$), 1.0 g (purity: 99.9 mol %) of I-iodoperfluorohexane ($C_6F_{13}I$), and 2.0 g of a fraction containing 1-iodoperfluorooctane ($C_8F_{17}I$).

The obtained first reaction mixture and second reaction mixture were subjected to compositional analysis by gas chromatography. The numbers of moles of 1-iodoperfluorohexane ($C_6F_{13}I$) with the degree of polymerization n of 2 and the number of moles of fluoroalkyl iodides with the degree of polymerization n of 3 or more were calculated firm gas chromatography compositional analysis results and the total amount of reactions containing 1-iodoperfluorohexane ($C_6F_{13}I$) and 1-iodoperfluorooctane ($C_8F_{17}I$) obtained from the first reaction mixture and second reaction mixture, which was calculated from the analysis results. The ratio of the number of moles of the fluoroalkyl iodides with the degree of polymerization n of 3 or more to the number of moles of 1-iodoperfluorohexane ($C_6F_{13}I$) with the degree of polymerization n of 2 was calculated as a percentage. Table 1 shows the results.

Example 2

A 200 ml-capacity stainless steel pressure reactor equipped with a stirrer was provided as a first reactor. The reactor was charged with 200 g of 1-iodoperfluoroethane ($C_2F_5I$) as a telogen and charged with 10 g of copper powder as a metal catalyst, followed by heating to 100° C. While the temperature in the reactor was maintained at 100° C., tetrafluoroethylene was supplied as a taxogen while stirring the reaction mixture to pressurize the reactor until the pressure in the reactor became 1.2 MPa (gauge pressure).

Then, while the above temperature and pressure conditions were maintained and while 1-iodoperfluoroethane ($C_2F_5I$) was supplied at a flow rate of 200 g/hr and tetrafluoroethylene was supplied at a flow rate of 5.0 g/hr, a reaction mixture was discharged from the reactor at a rate of 205.0 g/hr. A telomerization reaction was thereby performed. The obtained reaction mixture was cooled to give 2,254 g of a first reaction mixture.

This reaction mixture was distilled to yield 2,085 g (purity: 99.9 tool %) of 1-iodoperfluoroethane ($C_2F_5I$), 116 g (purity: 99.99 mol %) of 1-iodoperfluorobutane ($C_4F_9I$), 33 g (purity: 99.9 mol %) of 1-iodoperfluorohexane ($C_6F_{13}I$), and 12 g of a fraction containing 1-iodoperfluorooctaine ($C_8F_{17}I$).

A 200 ml-capacity stainless steel pressure reactor equipped with a stirrer was provided as a second reactor. The reactor was charged with 116 g of the above-prepared 1-iodoperfluorobutane ($C_4F_9I$) as a telogen and further charged with 5.8 g of copper powder as a metal catalyst. While the second reactor was heated such that the temperature in the reactor was maintained at 100° C., tetrafluoroethylene was supplied as a taxogen while stirring the reaction mixture to pressurize the reactor until the pressure in the reactor became 0.35 MPa (gauge pressure). Since the telomerization reaction consumed tetrafluoroethylene, the reaction was carried out while suitably supplying additional tetrafluoroethylene so as to keep the pressure constant. The supply of tetrafluoroethylene was stopped when a total of 4.2 g of tetrafluoroethylene was supplied, Cooling was performed to give a second reaction mixture, This reaction mixture was distilled to yield 100 g (purity: 99.9 mol %) of 1-iodoperfluorobutane ($C_4F_9I$), 13 g (purity: 99.9 mol %) of 1-iodoperfluorohexane ($C_6F_{13}I$), and 2.5 g of a fraction containing 1-iodoperfluorooctane ($C_6F_{17}I$).

The obtained first reaction mixture and second reaction mixture were subjected to compositional analysis by gas chromatography. The number of moles of 1-iodoperfluorohexane ($C_6F_{13}I$) with the degree of polymerization n of 2 and the number of moles of fluoroalkyl iodides with the degree of polymerization n of 3 or more were calculated from gas chromatography compositional analysis results and the total amount of fractions containing 1-iodoperfluorohexane ($C_6F_{17}I$) and 1-iodoperfluorooctane ($C_8F_{17}I$) obtained from the first reaction mixture and second reaction mixture, which was calculated from the analysis results. The ratio of the number of moles of fluoroalkyl iodides with the degree of polymerization n of 3 or more to the number of moles of 1-iodoperfluorohexane ($C_6F_{13}I$) with the degree of polymerization of 2 was calculated as a percentage. Table 1 shows the results.

Comparative Example 1

A 200 ml-capacity stainless steel pressure reactor equipped with a stirrer was provided. The reactor was charged with 200 g of 1-iodoperfluoroethane ($C_2F_5I$) as a telogen and charged with 10 g of copper powder as a metal catalyst, followed by heating to 120° C. While the temperature was maintained at 100° C., tetrafluoroethylene was continuously supplied as a taxogen while stirring the reaction mixture to pressurize the reactor until the pressure in the reactor became 1.20 MPa (gauge pressure).

Then, while the above temperature and pressure conditions were maintained, tetrafluoroethylene was supplied. The supply of tetrafluoroethylene was stopped when a total of 12.7 of tetrafluoroethylene was supplied. Cooling was performed to give a reaction mixture.

The obtained reaction mixture was subjected to compositional analysis by gas chromatography. The number of moles of 1-iodoperfluorohexane ($C_6F_{13}I$) with the degree of polymerization n of 2 and the number of moles of fluoroalkyl iodides with the degree of polymerization n of 3 or more in the reaction mixture were calculated from the analysis results. The ratio (%) of the number of moles of fluoroalkyl iodides with the degree of polymerization n of 3 or more to the number of moles of 1-iodoperfluorohexane ($C_6F_{13}I$) with the degree of polymerization n of 2 was calculated as the ratio (%) of fluoroalkyl iodides with the degree of polymerization n of 3 or more according to the following formula. Table 1 shows the results.

[Ratio (%) of fluoroalkyl iodides with the degree of polymerization $n$ of 3 or more]=[(Number of moles of fluoroalkyl iodides with the degree of polymerization $n$ of 3 or more)/(Number of moles of fluoroalkyl iodide with the degree of polymerization $n$ of 2)]×100

TABLE 1

|  | Example 1 | Example 2 | Comparative Example 1 |
|---|---|---|---|
| Reactor shape | Two chambers | Two chambers | Single chamber |
| Ratio (%) of fluoroalkyl iodides with the degree of polymerization n of 3 or more | 34.4 | 24.6 | 50.5 |

Results

When a fluoroalkyl iodide with the degree of polymerization n of 2 was produced by the production methods described in Examples 1 and 2, a plurality of reactors were used. In the first reactor, a reaction of 1-iodoperfluoroethane ($C_2F_5I$) with tetrafluoroethylene, which is a slow reaction, was performed to produce 1-iodoperfluorobutane ($C_4FYI$). In the second reactor, 1-iodoperfluorobutane ($C_4F_9I$) was reacted with tetrafluoroethylene to produce 1-iodoperfluorohexane ($C_6F_{13}I$). Therefore, the reaction in the second reaction, which is a fast reaction, can be independently performed from the slow reaction in the first reactor, thereby increasing the selectivity of the desired 1-iodoperfluorohexane ($C_6F_{13}I$).

In contrast, when a fluoroalkyl iodide with the degree of polymerization n of 2 was produced by the production method described in Comparative Example 1, 1-iodoperfluorobutane ($C_4F_9I$) and 1-iodoperfluorohexane ($C_6F_{13}I$) were produced at the same time in the single chamber reactor, which prolonged residence time and allowed consecutive reactions to proceed, thus increasing the ratio of fluoroalkyl iodides with the degree of polymerization n of 3 or more.

The invention claimed is:

1. A method for producing a mixture of fluoroalkyl iodides represented by formula (I):

$$R_f(CF_2CF_2)_nI \quad (I)$$

wherein $R_f$ represents a fluoroalkyl group having 1 to 10 carbon atoms, and n is an integer indicating a degree of polymerization, the degree of polymerization n being m or more, wherein m is an integer of 2 or more, by telomerization in metal catalyst-containing reactors, the method comprising:

(1) step 1 of reacting a fluoroalkyl iodide represented by formula (II):

$$R_fI \quad (II)$$

wherein $R_f$ is a fluoroalkyl group having 1 to 10 carbon atoms, with tetrafluoroethylene in the presence of a metal catalyst in a first reactor to obtain a first reaction mixture containing a mixture of fluoroalkyl iodides represented by formula (I) wherein the degree of polymerization n is 1 or more;

(2) step 2 of separating the first reaction mixture withdrawn from the first reactor into a first fraction containing a fluoroalkyl iodide or a mixture of fluoroalkyl iodides represented by formula (I) wherein the degree of polymerization n is (m−2) or less, a fluoroalkyl iodide represented by formula (II), and tetrafluoroethylene, a second fraction containing a fluoroalkyl iodide represented by formula (I) wherein the degree of polymerization n is (m−1), and a third fraction containing a mixture of fluoroalkyl iodides represented by formula (I) wherein the degree of polymerization n is m or more; and (3) step 3 of transferring the second fraction into a second reactor in which a metal catalyst is present and reacting the second fraction with tetrafluoroethylene in the second reactor to obtain a second reaction mixture containing a mixture of fluoroalkyl iodides represented by formula (I) wherein the degree of polymerization n is m or more.

2. The method according to claim 1, which produces a mixture of fluoroalkyl iodides represented by formula (I) wherein $R_f$ represents $C_2F_5$ and n is 2 or more.

3. The method according to claim 1, wherein step 1 further comprises returning the first fraction separated in step 2 to the first reactor to supply one or more types of fluoroalkyl iodides represented by formula (I) wherein the degree of polymerization n is (m−2) or less and tetrafluoroethylene, and reacting the one or more types of fluoroalkyl iodides with the tetrafluoroethylene.

4. The method according to claim 1, further comprising step 4 of separating the second reaction mixture obtained in step 3 into a fourth fraction containing a fluoroalkyl iodide or a mixture of fluoroalkyl iodides represented by formula (I) wherein the degree of polymerization n is (m−1) or less, and tetrafluoroethylene, a fifth fraction containing a fluoroalkyl iodide represented by formula (I) wherein the degree of polymerization n is m, and a sixth fraction containing a mixture of fluoroalkyl iodides represented by formula (I) wherein the degree of polymerization n is (m+1) or more.

5. The method according to claim 4, wherein the third fraction separated in step 2 is subjected to step 4 together with the second reaction mixture to supply to step 4 a mixture of fluoroalkyl iodides represented by formula (I) wherein the degree of polymerization n is m or more.

6. The method according to claim 4, wherein when a cycle comprising subjecting the second fraction to steps 3 and 4 to obtain a fifth fraction, which is a next fraction, is defined as one cycle, the next fraction obtained by the cycle is further subjected to the same steps as steps 3 and 4 to thereby repeat the cycle p times, wherein p is an integer of 1 or more.

7. The method according to claim 1, wherein the metal catalyst is at least one member selected from the group consisting of copper, zinc, magnesium, vanadium, rhenium, rhodium, ruthenium, platinum, silver, and these metals with a small amount of a transition metal added thereto.

8. The method according to claim 2, wherein step 1 further comprises returning the first fraction separated in step 2 to the first reactor to supply one or more types of fluoroalkyl iodides represented by formula (I) wherein the degree of polymerization n is (m−2) or less and tetrafluoroethylene, and reacting the one or more types of fluoroalkyl iodides with the tetrafluoroethylene.

9. The method according to claim 2, further comprising step 4 of separating the second reaction mixture obtained in step 3 into
- a fourth fraction containing a fluoroalkyl iodide or a mixture of fluoroalkyl iodides represented by formula (I) wherein the degree of polymerization n is (m−1) or less, and tetrafluoroethylene,
- a fifth fraction containing a fluoroalkyl iodide represented by formula (I) wherein the degree of polymerization n is m, and
- a sixth fraction containing a mixture of fluoroalkyl iodides represented by formula (I) wherein the degree of polymerization n is (m+1) or more.

10. The method according to claim 3, further comprising step 4 of separating the second reaction mixture obtained in step 3 into
- a fourth fraction containing a fluoroalkyl iodide or a mixture of fluoroalkyl iodides represented by formula (I) wherein the degree of polymerization n is (m−1) or less, and tetrafluoroethylene,
- a fifth fraction containing a fluoroalkyl iodide represented by formula (I) wherein the degree of polymerization n is m, and
- a sixth fraction containing a mixture of fluoroalkyl iodides represented by formula (I) wherein the degree of polymerization n is (m+1) or more.

11. The method according to claim 2, wherein the metal catalyst is at least one member selected from the group consisting of copper, zinc, magnesium, vanadium, rhenium, rhodium, ruthenium, platinum, silver, and these metals with a small amount of a transition metal added thereto.

12. The method according to claim 3, wherein the metal catalyst is at least one member selected from the group consisting of copper, zinc, magnesium, vanadium, rhenium, rhodium, ruthenium, platinum, silver, and these metals with a small amount of a transition metal added thereto.

13. The method according to claim 4, wherein the metal catalyst is at least one member selected from the group consisting of copper, zinc, magnesium, vanadium, rhenium, rhodium, ruthenium, platinum, silver, and these metals with a small amount of a transition metal added thereto.

14. The method according to claim 5, wherein the metal catalyst is at least one member selected from the group consisting of copper, zinc, magnesium, vanadium, rhenium, rhodium, ruthenium, platinum, silver, and these metals with a small amount of a transition metal added thereto.

15. The method according to claim 6, wherein the metal catalyst is at least one member selected from the group consisting of copper, zinc, magnesium, vanadium, rhenium, rhodium, ruthenium, platinum, silver, and these metals with a small amount of a transition metal added thereto.

* * * * *